United States Patent [19]

Rogberg et al.

[11] Patent Number: 5,236,539
[45] Date of Patent: Aug. 17, 1993

[54] APPARATUS FOR LAYING ELASTIC THREAD ON A WEB OF MATERIAL

[76] Inventors: John A. Rogberg, Krokslatts Parkg. 49, S-431 68 Molndal; Verner E. Andersen, Lingonvagen 11A, S-435 00 Molnlycke, both of Sweden

[21] Appl. No.: 582,940
[22] PCT Filed: Apr. 10, 1989
[86] PCT No.: PCT/SE89/00189
§ 371 Date: Dec. 20, 1990
§ 102(e) Date: Dec. 20, 1990
[87] PCT Pub. No.: WO89/09550
PCT Pub. Date: Oct. 19, 1989

[30] Foreign Application Priority Data

Apr. 11, 1988 [SE] Sweden ................................. 8801324

[51] Int. Cl.$^5$ ................ A41B 13/00; A61F 13/15
[52] U.S. Cl. ........................... 156/495; 156/440; 156/494; 156/164; 156/229; 604/385.2
[58] Field of Search ............... 156/229, 164, 494, 495, 156/496, 291, 439, 440; 604/385.2

[56] References Cited

U.S. PATENT DOCUMENTS

| | | |
|---|---|---|
| 3,828,367 | 8/1974 | Bourgeois . |
| 4,020,194 | 4/1977 | McIntyre et al. ............... 156/291 X |
| 4,081,301 | 3/1978 | Buell ..................... 156/164 |
| 4,216,687 | 8/1980 | Passafiume et al. |
| 4,293,367 | 10/1981 | Klasek et al. .......... 156/494 |
| 4,297,157 | 10/1981 | Van Vliet . |
| 4,479,836 | 10/1984 | Dickover et al. ............ 156/495 X |
| 4,585,507 | 4/1986 | Bradley et al. ............... 156/494 X |
| 4,642,109 | 2/1987 | Bradley et al. . |
| 4,675,068 | 6/1987 | Lundmark ......................... 156/495 |
| 4,801,345 | 1/1989 | Dussaud ........................ 156/164 |
| 4,915,767 | 4/1990 | Rajala et al. .................... 156/164 X |
| 4,917,746 | 4/1990 | Kons et al. ..................... 156/495 X |

FOREIGN PATENT DOCUMENTS

| | | |
|---|---|---|
| 0048010 | 3/1982 | European Pat. Off. . |
| 0183662 | 2/1989 | European Pat. Off. . |
| 449820 | 5/1987 | Sweden . |
| 2123272 | 2/1984 | United Kingdom . |

Primary Examiner—Jeff H. Aftergut
Attorney, Agent, or Firm—Young & Thompson

[57] ABSTRACT

An apparatus for laying pre-stretched elastic threads in a curved path on a continuously advancing web of material includes at least one rotatable thread-guide roll. The roll is provided with a peripherally extending curved groove or slot whose axial amplitude controls the positioning of the threads on the web, and achieves the desired curvature of the threads. The apparatus further includes a glue applicator for applying adhesive to the threads. The roll may conveniently have the form of a tube provided with through passing slots for guiding the threads straight through the tube and laying them onto the web.

8 Claims, 6 Drawing Sheets

APPARATUS FOR LAYING ELASTIC THREAD ON A WEB OF MATERIAL

FIELD OF THE INVENTION

The present invention relates to a method of laying out pre-stretched elastic thread in curves on a continuously advancing web of material, preferably a layer of material which will form part of a diaper, said threads being intended to serve as leg elastic. The invention also relates to apparatus for carrying out the method.

BACKGROUND OF THE INVENTION

It is known in the manufacture of so-called disposable diapers to provide the diapers with elastic in order to elasticate the leg portions of the diapers and therewith hold said leg portions around the thighs of the wearer. An example of diapers of this kind is, described and illustrated in U.S. patent specification No. 3,860,003. These diapers have absorption pads or bodies of an hour-glass configuration, with which the narrower center part, intended to conform to the shape of the body, forms the crotch part of the diaper when the diaper is in use. However, elastic threads which are positioned rectilinearly and parallel with the longitudinal axis of the diaper tend to result in chafing of the skin of the wearer in the crotch region.

It is also known to apply elastic in a V-shaped pattern, where the elastic intersects the absorption pad in the vicinity of the crotch portion of the diaper. A diaper in which the elastic is positioned in this fashion will conform to the shape of the body more satisfactorily than the diaper of the aforesaid U.S patent, and also avoids irritating chafing of the crotch area in use.

It is also known to arrange the elastic threads in a network of threads, such as to provide a curved leg elastic in a manner similar to that found with tailor sewn leg apparel or garments. One method of providing such elastic is described in our Swedish Patent Specification 8406071-4.

For the purpose of laying out elastic threads in a curved path on a continuously advancing web of material, it is conceivable, for instance, to guide the thread applicator electrically, to and fro in the transverse direction of the web. Such manufacture, involving rapid transverse movements, is complicated, however, particularly in the case of high speed manufacture.

SUMMARY OF THE INVENTION

The present invention provides apparatus by means of which elastic threads can be placed in curved paths in a simple, efficient and speedy manner with the use of only a few movable parts.

The method for operating the inventive apparatus is characterized in that the threads are fed guided through or along curved grooves or slots provided in one more rotating rolls and are steered by the rolls as they are laid out onto said web, and that the threads are then bonded to the web with the aid of an adhesive The apparatus for carrying out the method is characterized by at least one rotatable roll which is provided with a peripherally extending curved groove or slot, the axial amplitude of which controls the positioning of the threads on the material layer and achieves the desired curvature of the threads, and by a glue applicator for applying adhesive to the threads.

The roll may conveniently have the form of a tube provided with through passing slots for guiding the threads straight through the tube and laying the threads onto the material surface.

BRIEF DESCRIPTION OF THE DRAWINGS

The invention will now be described in more detail with reference to an embodiment thereof illustrated in the accompanying drawings, in which.

DETAILED DESCRIPTION OF THE INVENTION

Figure 1:
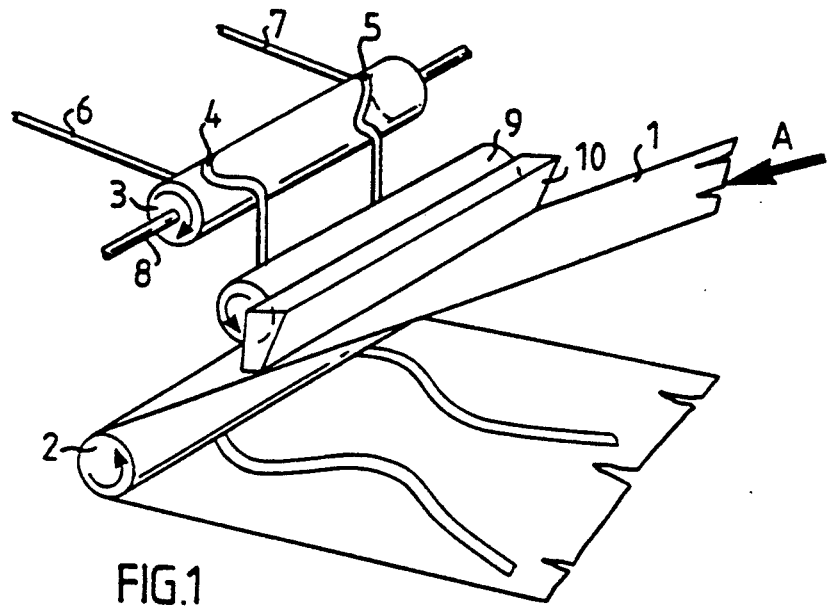
FIG. 1 illustrates schematically and in perspective the positioning of elastic threads on a layer of material in a diaper manufacturing process.

In FIG. 1, a web of material 1 is advanced over a web deflecting roll 2 in the direction of the arrow A. The reference numeral 3 identifies a hollow roll. The roll 3 is provided with through-passing curved slots 4, 5 through which elastic threads 6, 7 are fed towards the deflecting roll 2, for positioning on the web 1. The roll 3 is driven in its direction of rotation by a drive shaft 8, which supports the roll at the ends thereof and on both sides of respective slots. The axial amplitude of the slots guides the positioning of the threads on the web 1, in a manner to obtain the desired thread curvature. A glue roller 9 is provided for applying glue taken from a tray 10 onto the elastic threads, which are bonded to the web 1 as it passes the deflecting roll 2. The extension of the threads on the web I has been shown in FIG. 1. The threads are held in their illustrated pattern by the tension in the web 1.

In FIG. 1 there has been shown a single rotating roll provided with two through-passing slots. It will be understood, however, that the roll may comprise two separate roll parts with a slot in each part, and that the roll parts may be arranged for mutual displacement in their axial directions, thereby enabling the positioning of each thread to be guided separately. This embodiment is illustrated schematically in FIG. 2, in which the two roll parts are referrenced 3' and 3".

Figure 2:
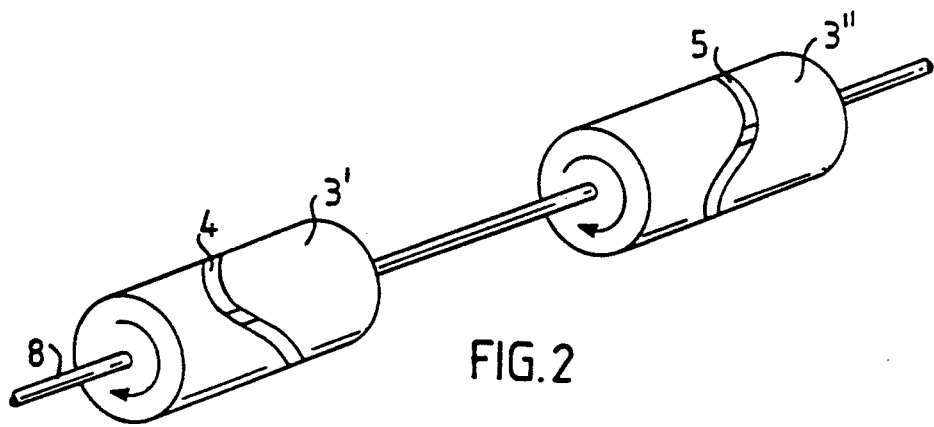
FIG. 2 illustrates part of the apparatus shown in FIG. 1, said apparatus being a modified version of that in FIG. 1.

Although not shown, the roll according to FIG. 1 and the roll parts according to FIG. 2 may be provided with more slots, so as to enable more parallel threads to be laid out.

Figure 3:
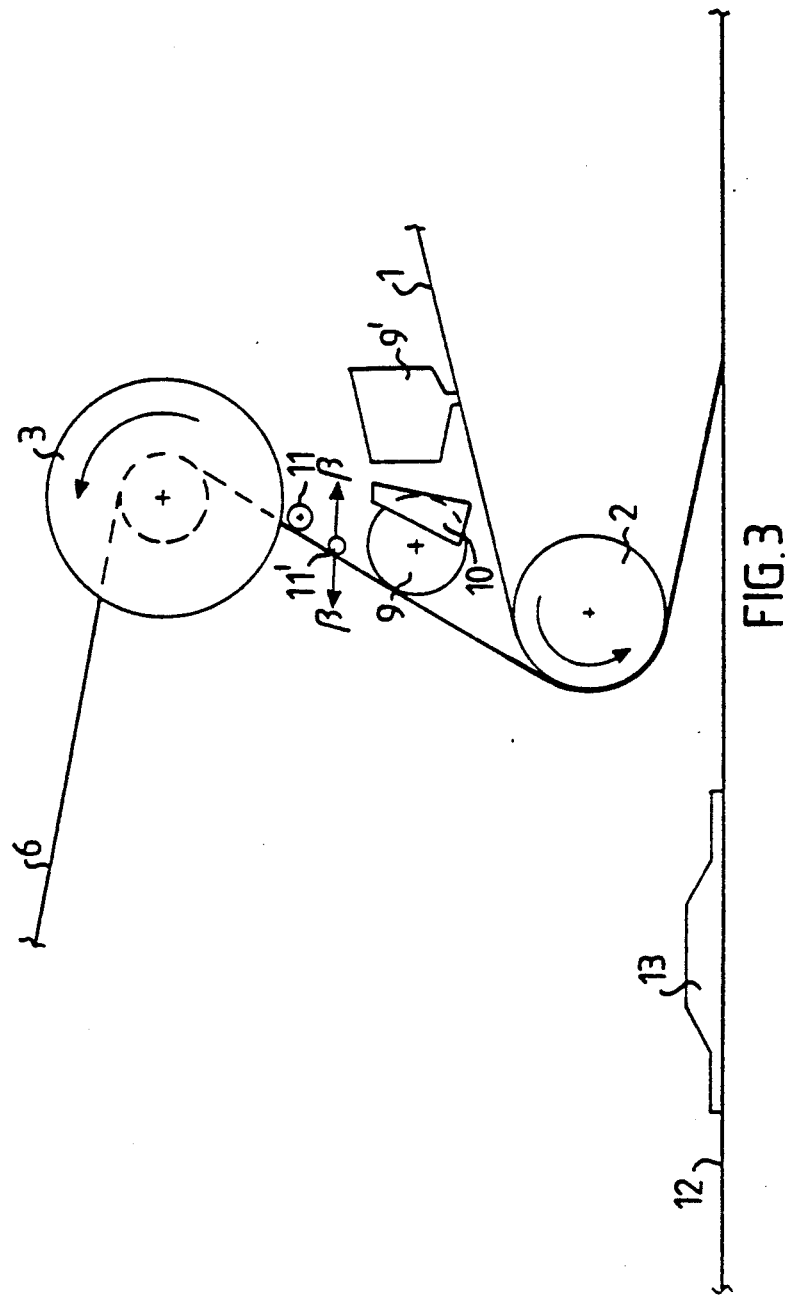
FIG. 3 illustrates a method of intermittently gluing the elastic threads.

FIG. 3 illustrates a slightly modified version of the embodiment shown in FIG. 1. Those parts in FIG. 3 which have correspondence in the FIG. 1 embodiment have been identified with like references. In the case of this modified version, a brake roll 11 is located downstream of the exit from the roll slots and functions to prevent the occurrence of undesirable thread lengths.

Mounted between the brake roll 11 and the glue applicator roller 9 is a lifting device 11' which is capable of moving in the direction of arrows B. The lifting device is intended for lifting the elastic threads out of engagement with the glue applying roll at regular intervals, thereby achieving intermittent gluing of the threads 6, 7 to the material web 1.

FIG. 3 illustrates schematically the manufacture of a coherent web of disposable diapers. The web comprises a liquid permeable fibre layer or fabric which is intended to form the outer layer of the diaper. A web of plastic film 12 is advanced beneath the deflecting roll 2, this plastic film forming the other and liquid impervious layer or backing sheet of said diaper. Uniformally spaced on the web of plastic film 12 are absorption bodies or pads 13, which have been formed in a conventional manner, by air-laying fluff pulp in forms (not shown). The two material layers are brought together around the absorption pads in a conventional manner (not shown) and the web is cut appropriately, to produce individual diapers. Adhesive for bonding together the two layers of material is applied with the aid of a glue supply device 9'.

Figure 4:
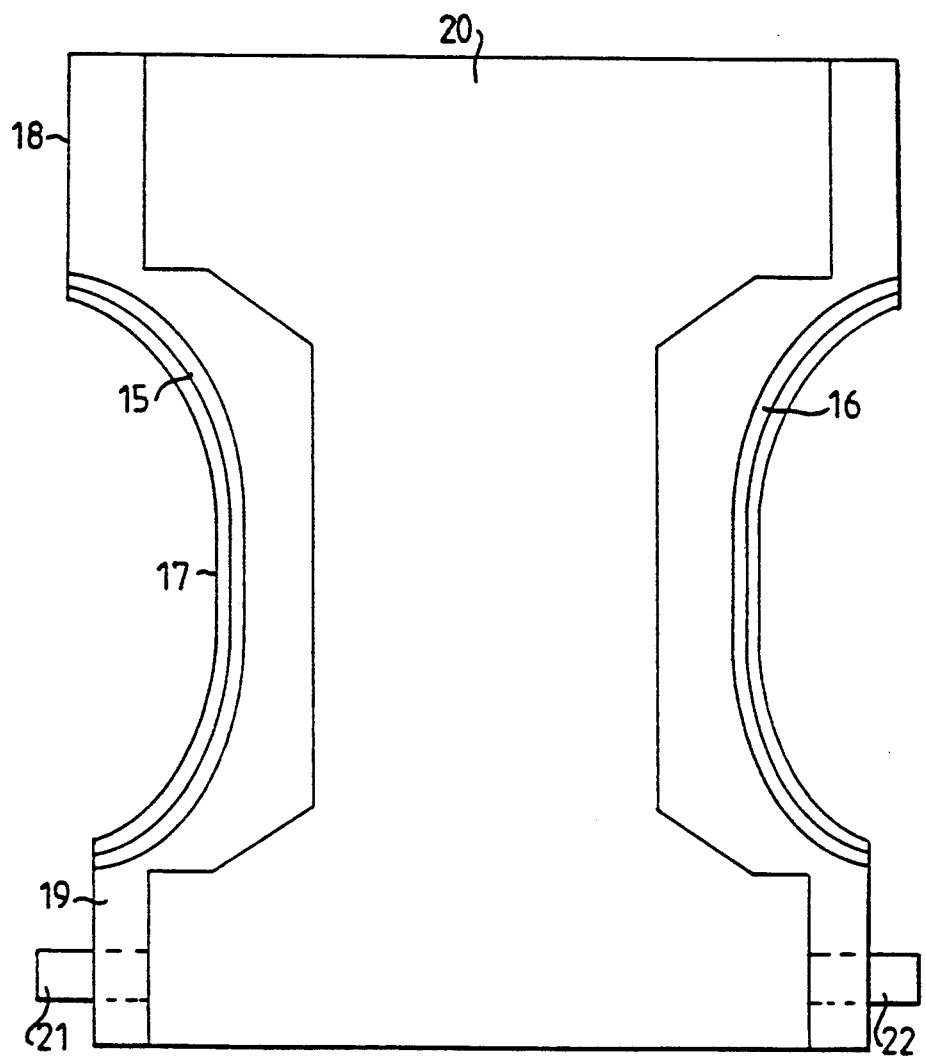
FIG. 4 illustrates a diaper manufactured by means of the inventive apparatus.

FIG. 4 illustrates by way of example a diaper capable of being manufactured by means of the inventive apparatus. The illustrated diaper 14 has an hour-glass configuration and the elastic threads 15, 16 are placed in an arcuate path solely in the crotch region 17 of the diaper. The waist portions of the diaper are referenced 18, 19. The diaper includes an absorbent core 20 and a casing which envelops the core and which extends laterally beyond the absorption pad. The diaper is secured with the aid of adhesive tape fasteners 21, 22. This intermittent application of the elastic threads has been made possible because parts of the threads have been guided laterally by the thread-guide roll beyond the actual diaper itself and have been severed as the individual diapers are cut from the coherent diaper web.

Figure 5:
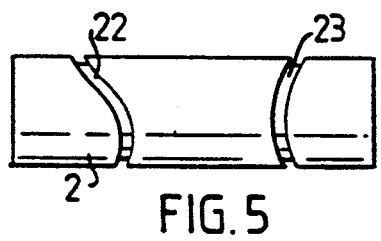
FIG. 5 illustrates a deflecting roll which is a modification of the embodiments shown in FIGS. 1 and 3.

FIG. 5 illustrates a deflecting roll 2 which is a slightly modified version of the deflecting roll of the embodiments illustrated in FIGS. 1 and 3. This modified roll 2 is provided with narrow peripheral, curved grooves 22, 23 whose amplitudes correspond to the desired curvature of the elastic. Because the threads are pressed down into the grooves there is obtained a larger glue surface between the threads and the plastic film.

Figure 6:
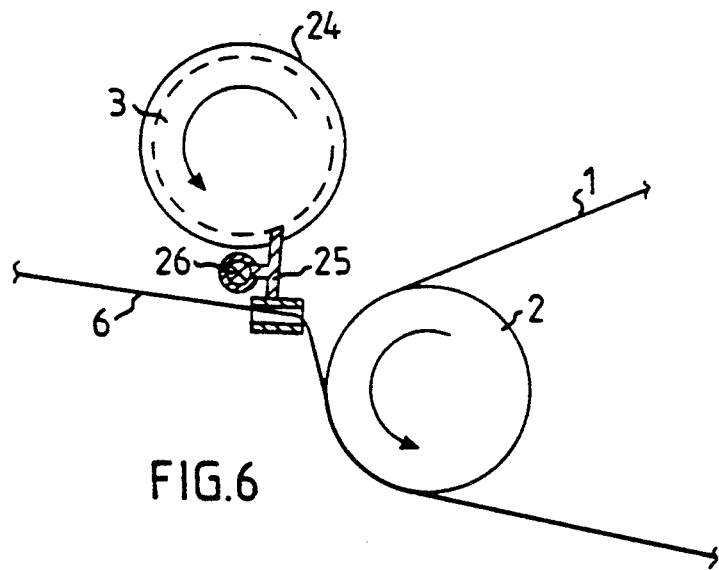
FIG. 6 illustrates a further embodiment of the invention.

FIG. 6 illustrates an embodiment which has a thread-guide roll of different configuration. This roll is provided with curved grooves 24 whose axial amplitudes correspond to the desired curvature of the threads on the material web. Thread guiding devices 25 are mounted for axial displacement along a shaft 26 which extends parallel with the thread-guide roll. The thread guiding devices 25 are mounted for movement along the grooves 24 and are guided by said grooves along the shaft 26. The elastic threads 6 run through the thread guiding devices and are guided thereby, as they are laid onto the material web 1.

Figure 7:
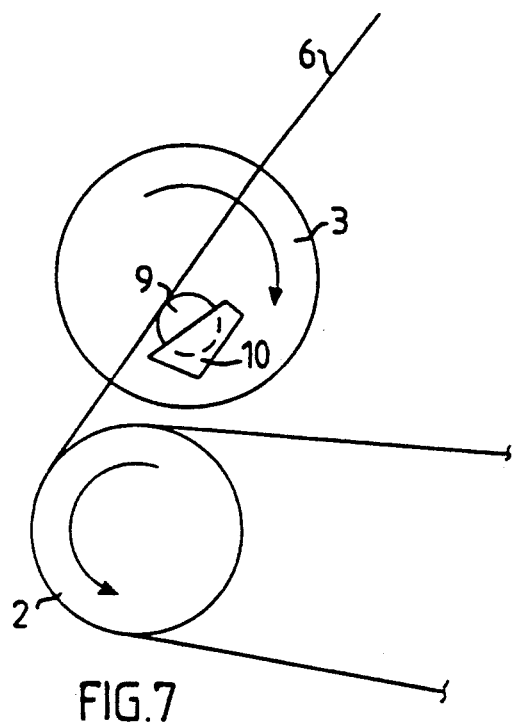
FIG. 7 illustrates an embodiment in which the glue applicator is located within the thread-guide roll.

FIG. 7 illustrates a further embodiment of the thread-guide roll. This roll comprises a hollow tube which has arranged therein a glue applying roller 9 and a glue tray 10, which is stationary in relation to the tube. The purpose of this embodiment is to shorten the distance from the thread-guide roll to the deflecting roll. The shorter this distance is, the more accurately the threads are laid.

Figure 8:
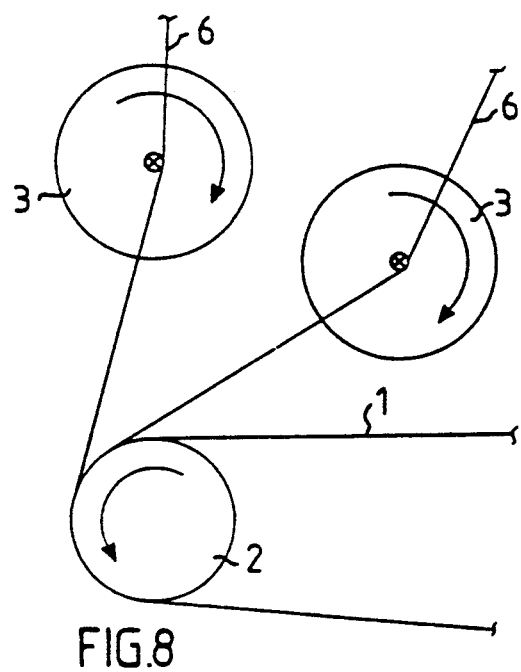
FIG. 8 illustrates a method of applying a plurality of threads.

FIG. 8 illustrates an embodiment which comprises two separate and mutually parallel thread-guide rolls. This embodiment will enable a larger number of threads to be laid out on the web.

Figure 9:
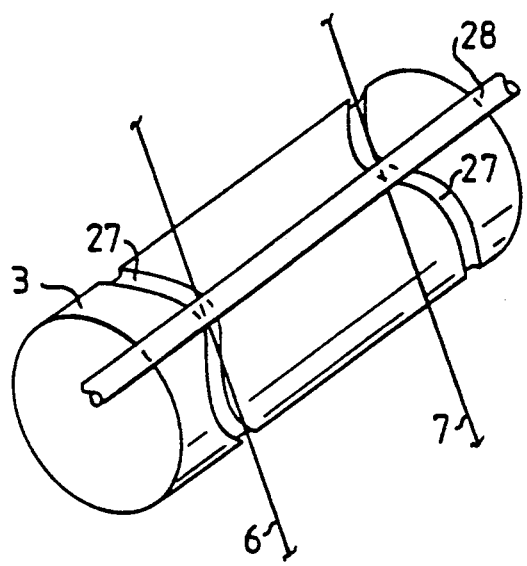
FIG. 9 illustrates an alternative embodiment of a thread-guide roll.

FIG. 9 illustrates a further embodiment of the thread-guide roll. The roll of this embodiment is provided with peripheral grooves 27 which are intended to guide the positioning of the threads. The elastic threads are held in the grooves 27 by means of a guide strap 28 which lies against the periphery of the thread-guide roll.

It will be understood that the invention is not restricted to the described and illustrated embodiments thereof and that modifications can be made within the scope of the following claims.

For example, the thread-guide rolls may be provided with grooves of different configurations to those described so as to enable elastic threads to be positioned in other patterns or shapes on the web.

Furthermore, in the case of embodiments intended for positioning a plurality of threads on the web, means may be provided for imparting mutually different tensions to mutually different elastic threads.

In the case of the FIG. 9 embodiment, the strap 28 can be replaced with a rotatable shaft, which will therewith decrease the friction on the elastic threads 6, 7.

We claim:

1. Apparatus for laying pre-stretched elastic threads in a curved path on a continuously advancing web of material, said apparatus comprising: at least one rotatable thread-guide roll having curved slots provided around its periphery and a glue supply device for supplying glue in a manner to bond the threads to the web of material, said thread-guide roll comprising a tube having an interior and provided with through passing slots for guiding the threads from an inlet point through the interior of the tube to an outlet point when laying the threads onto the web of material, and wherein an axial position of the threads at the inlet and outlet points are varied in accordance with the curvature of the slots during rotation of the tube.

2. Apparatus according to claim 1, wherein the web of material is a layer of material forming part of a diaper, and the threads are intended to function as leg elastics, and wherein the circumference of the thread-guide roll corresponds to a length of a diaper.

3. Apparatus according to claim 2, wherein the thread-guide roll comprises two mutually separate and two mutually displaceable roll parts, which when laying out at least one thread on each edge of the layer material, are effective in guiding each thread separately along respective edges.

4. Apparatus according to claim 1, further including a brake roll downstream of the outlet point from the slots, said brake roll being effective for preventing the laying of threads of undesirable lengths.

5. Apparatus according to claim 1, further including a web deflecting roll at which the threads are applied to the web subsequent to leaving the thread-guide roll.

6. Apparatus according to claim 5, wherein the deflecting roll is provided with shallow thread-accommodating grooves, therewith causing part of the web to surround the threads and providing a larger glue area.

7. Apparatus according to claim 1, wherein the glue supply device includes a glue applicating roller, and means for intermittently moving the threads out of engagement with the glue applicating roller for achieving intermittent gluing of the threads.

8. Apparatus according to claim 7, wherein the glue applicating roller is located in the interior of the tube.

* * * * *